(12) United States Patent
Layus et al.

(10) Patent No.: US 11,497,777 B2
(45) Date of Patent: Nov. 15, 2022

(54) COMPOSITION COMPRISING A MIXTURE OF BACILLUS SUBTILIS AND LACTIC ACID BACTERIUM INTENDED FOR IMPROVING THE HEALTH OF YOUNG OVIPAROUS ANIMALS

(71) Applicant: MIXSCIENCE, Bruz (FR)

(72) Inventors: Michel Layus, Pleumeur Bodou (FR); Alexandre Brame, Rennes (FR)

(73) Assignee: MIXSCIENCE, Bruz (FR)

( * ) Notice: Subject to any disclaimer, the term of this patent is extended or adjusted under 35 U.S.C. 154(b) by 131 days.

(21) Appl. No.: 16/954,885

(22) PCT Filed: Dec. 21, 2018

(86) PCT No.: PCT/EP2018/086643
§ 371 (c)(1),
(2) Date: Jun. 17, 2020

(87) PCT Pub. No.: WO2019/122356
PCT Pub. Date: Jun. 27, 2019

(65) Prior Publication Data
US 2020/0397836 A1 Dec. 24, 2020

(30) Foreign Application Priority Data
Dec. 22, 2017 (FR) ..................... 17/63192

(51) Int. Cl.
| | | |
|---|---|---|
| *A61K 35/742* | (2015.01) | |
| *A61K 35/747* | (2015.01) | |
| *A23K 50/75* | (2016.01) | |
| *A23K 10/18* | (2016.01) | |
| *A01K 61/17* | (2017.01) | |
| *A01K 61/59* | (2017.01) | |
| *A01K 41/00* | (2006.01) | |
| *A01K 45/00* | (2006.01) | |
| *A01K 61/00* | (2017.01) | |

(52) U.S. Cl.
CPC ............ *A61K 35/742* (2013.01); *A01K 41/00* (2013.01); *A01K 45/007* (2013.01); *A01K 61/00* (2013.01); *A01K 61/17* (2017.01); *A01K 61/59* (2017.01); *A23K 10/18* (2016.05); *A23K 50/75* (2016.05); *A61K 35/747* (2013.01)

(58) Field of Classification Search
None
See application file for complete search history.

(56) References Cited

U.S. PATENT DOCUMENTS 9,980,989 B2 * 5/2018 De Brueker .............. A23L 2/38

FOREIGN PATENT DOCUMENTS

| EP | 1472933 A1 | 11/2004 |
|---|---|---|
| WO | WO 98/54981 A1 | 12/1998 |
| WO | WO 2013/178947 A1 | 12/2013 |
| WO | WO 2017/132230 A1 | 8/2017 |

OTHER PUBLICATIONS

International Search Report dated Mar. 27, 2019 issued in PCT/EP2018/086643.
Giarma Eleni et al. "Defense systems in developing Artemia franciscana nauplii and their modulation by probiotic bacteria offer protection against a Vibrio anguillamm challenge" Fish & Shellfish Immunology, vol. 66, Jul. 2017 (Jul. 2017), pp. 163-172.
Mohapatra Sipra et al. "Dietary Multispecies Probiotic Supplementation Enhances the Immunohematological Responses and Reduces Mortality by Aeromonas hydrophila in Labeorohita Fingerlings" Journal of the World Aquaculture Society, vol. 45, No. 5, Oct. 2014 (Oct. 2014), pp. 532-544.

* cited by examiner

*Primary Examiner* — Vera Afremova
(74) *Attorney, Agent, or Firm* — Scully, Scott, Murphy & Presser, P.C.

(57) ABSTRACT

The invention relates to a composition comprising a mixture of at least one strain of a bacterium of the genus *Bacillus* and at least one strain of lactic acid bacterium for use in the prevention of infections in farmed oviparous animals.

7 Claims, 2 Drawing Sheets

[Fig. 1]
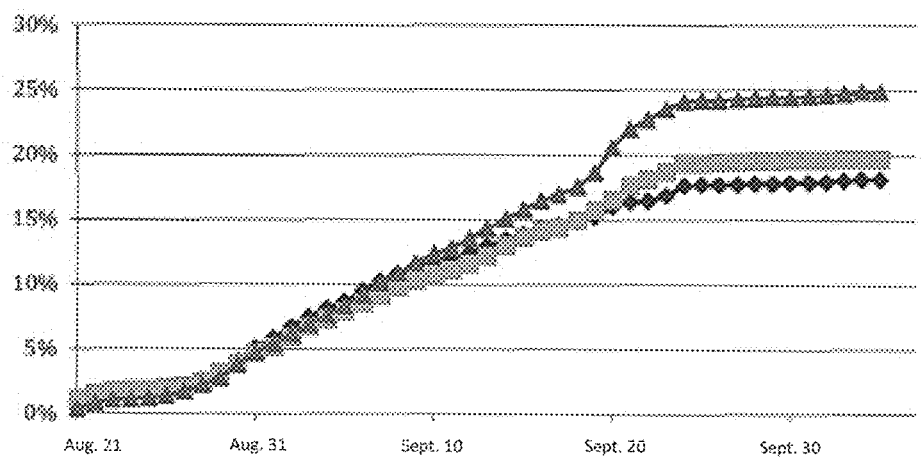
[Fig. 2]
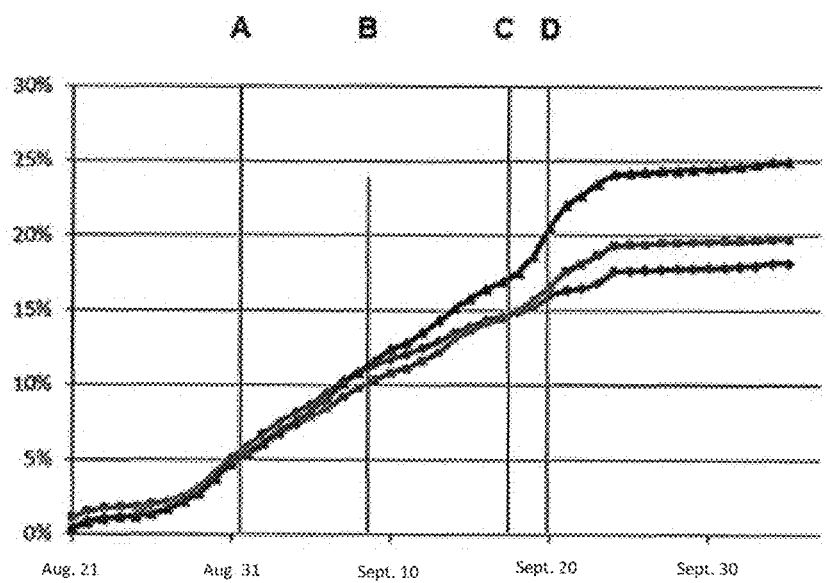
[Fig. 3]
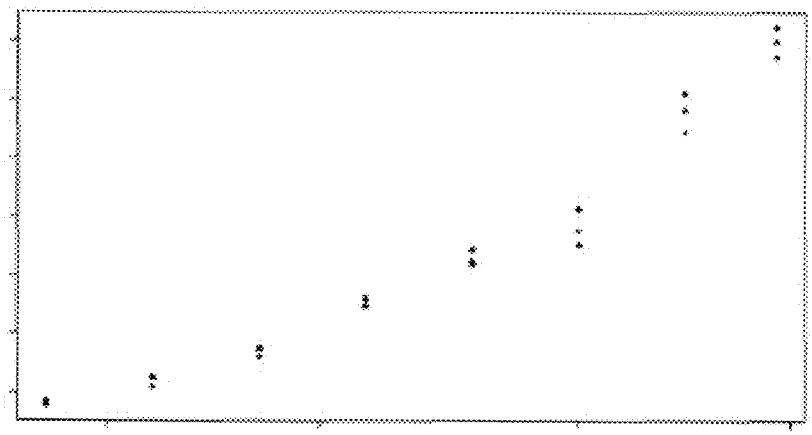

[Fig. 4]
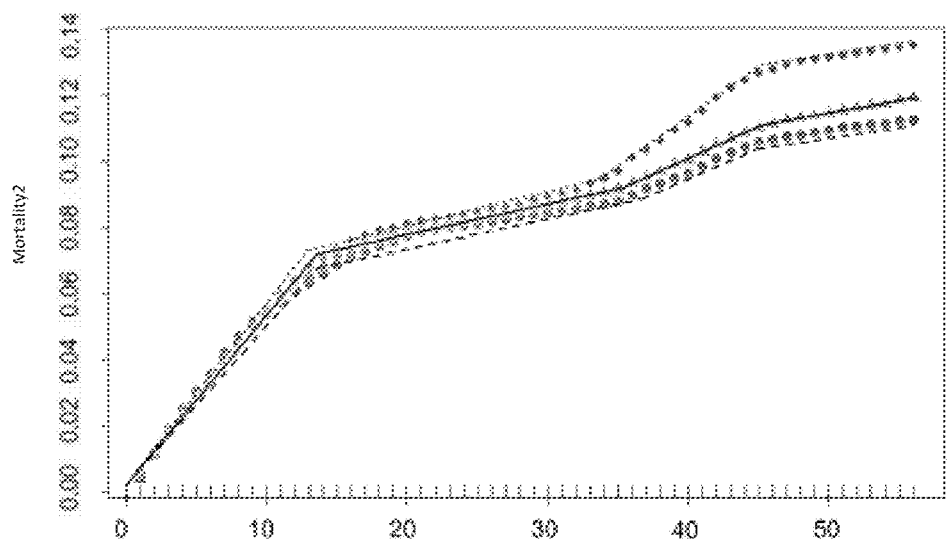

COMPOSITION COMPRISING A MIXTURE OF BACILLUS SUBTILIS AND LACTIC ACID BACTERIUM INTENDED FOR IMPROVING THE HEALTH OF YOUNG OVIPAROUS ANIMALS

The invention relates to a composition intended to improve the health of oviparous animals, and in particular young oviparous animals.

The inside of the eggs of oviparous animals is sterile if the integrity of the egg is preserved. During hatching, the first microbism in contact with the young oviparous animal will therefore be that present on the egg. This first contact with microbes corresponds to the first step in the formation process of the microbial ecosystem of the oviparous animals, which will continue through the contact with the ecosystem of the living environment and the food of the young animals.

However, contamination by a pathogenic microorganism is therefore possible as of hatching. During the first moments of life, the microbisms of the young oviparous animals and their immune systems being in formation, the latter are very vulnerable to pathogens.

The biocontrol of microbial ecosystems outside the egg, of the environment of young oviparous animals and of the food therefore appears crucial to avoid the risks of contamination of these animals and to encourage proper formation of their microbism.

Decision-makers are asking animal food producers, farmers, veterinarians and regulating bodies to work together to decide on best breeding and hygiene practices and viable alternatives, in order to reduce the use of antibiotics in farmed animals and to improve the well-being of the animals.

In order to meet the new requirements of modern agriculture, and taking into account the biological constraints of oviparous animals, it is necessary to develop new methods for preventing the contamination of young animals.

The methods known from the prior art in particular seek to treat the rearing environment of young oviparous animals in order to encourage their growth and well-being. For example, application WO 2017/132230 describes spraying probiotics only on young chicks after hatching in order to increase zootechnical performance levels in poultry farming.

Other methods known from the prior art in turn seek to influence performance levels through the diet of the young oviparous animals. Application EP 1,472,933 A1 is for example known, which describes a food composition intended to improve fish health. International application WO 98/54981 in turn seeks to supplement bacterial flora in the early stage of poultry development.

However, these methods do not account for the biocontrol of the microbism of eggs, which is nevertheless crucial in the formation process of the microbiota of young oviparous animals.

The invention therefore aims to address this drawback.

One aim of the invention is to propose a method for preventing health risks and improving the performance levels of farmed oviparous animals, as well as a microbial composition.

The invention therefore relates to a composition comprising or essentially consisting of a mixture of:
 a. at least one strain of a bacterium of the genus *Bacillus*, in particular a strain of *Bacillus subtilis*, and
 b. at least one strain of lactic acid bacterium,
for the use thereof in the prevention of infections or the improvement of zootechnical performance levels, in particular in the first days after hatching, in farmed oviparous animals,
said composition being placed in direct contact with the eggs of said farmed oviparous animals.

The invention is based on the surprising observation by the inventors that an application of a bacterial composition comprising strains of *Bacillus* and lactic acid bacteria, applied directly on the eggs of oviparous animals, makes it possible to improve the health of the newborns of oviparous animals substantially, and to protect them, from a very young age (as of hatching), from infections that are harmful to their development, and thus to promote and improve their growth.

The composition as used in the invention has the advantage of acting internally within the animal and in its outside environment, making it possible to create a barrier flora from a very early age.

Within the meaning of the invention, "egg" refers to a living cell, surrounded by food reserves and protective enclosures, that will be given to a young animal of a given species.

Within the meaning of the invention, "biocontrol" refers to orientating a population by promoting and/or limiting the development of certain microbial species in a given microbial ecosystem, by using microorganisms or natural substances. Reference is for example made to biocontrol of the microbial ecosystem of the rearing environment, biocontrol of the microbial ecosystem of the food or biocontrol of the intestinal microbial ecosystem.

The oviparous animals according to the invention are animals that lay fertilized or unfertilized eggs, the hatching of which occurs outside the body of the animal, that is to say, animals for which all or part of the embryonic development, optionally including fertilization, occurs outside the body of the animal.

Within the meaning of the invention, "zootechnical performance levels" refer to the quantitative indicators for evaluating the biological aptitude of the animal for the production for which it is reared. These indicators are in particular weight-related performance levels (weight, average daily gain, consumption index, etc.), reproduction performance levels (fertility, fecundity, prolificity, hatching rate, etc.) or production performance levels strictly speaking (meat production, rate of lay, mortality, etc.).

Within the meaning of the invention, "the first days after hatching" defines the hatching and the following days, in particular the first 5 days after leaving the egg.

For species having an average farmed lifetime of less than one year, the first days after hatching may reach up to 30 days. For species having a farmed lifetime of more than one year, this period may reach up to 2 months.

More specifically, the first days after hatching include the moment where the newborn leaves the egg in which its embryonic development occurred.

The composition according to the invention is used in direct contact with the egg of farmed oviparous animals, that is to say, the composition according to the invention is applied either on the eggs by spraying, incubation, soaking, spreading or powder dusting, or in the incubation environment of the eggs of the oviparous animals (substrate or surfaces of the incubators, brooders, hatchery and any other rearing equipment (in particular tubs, carriages, drawers, trays, screens, etc. in contact with the eggs before hatching).

Applying the composition according to the invention directly on the eggs makes it possible to cover the eggs with the solution, and thus to orient and/or control the bacterial flora present on the surface of the eggs.

The aim is for the composition according to the invention to be on the egg or in contact with the egg.

In the invention, the eggs that are covered with the aforementioned composition are eggs placed in a brooder or incubator (or in an aquaculture hatchery: tank). The brooder, incubator or hatchery is the location where the eggs are placed to keep them at ideal temperatures for embryonic development. These eggs can in particular be isolated from the adult animals.

It is particularly advantageous in the invention for the aforementioned composition to comprise at least two strains of *Bacillus*, and in particular at least two different strains of *Bacillus* and at least one strain of lactic acid bacterium, in particular *Lactococcus lactis*.

It is still more advantageous in the invention for the aforementioned composition to comprise at least three strains of *Bacillus*, and in particular at least three different strains of *Bacillus*, and at least one strain of lactic acid bacterium, in particular of *Lactococcus lactis*.

It is still more advantageous in the invention for the aforementioned composition to comprise at least four strains of *Bacillus*, and in particular at least four different strains of *Bacillus* and at least one strain of lactic acid bacterium, in particular of *Lactococcus lactis*.

Aside from improving the zootechnical performance levels, the composition according to the invention is used to prevent infections in farmed oviparous animals. The infections of said farmed oviparous animals are in particular infections due to the proliferation of bacteria or pathogenic viruses such as: *Aeromonas salmonicida, Edwarsiella tarda, Flavobacterium* spp *Photobacterium damsela damsela, Stretococcus iniae, Streptococcus dysgalactiae, Streptococcus agalactiae, Tenacibaculum discolor, Tenacibaculurn maritimum, Vibrio alginolyticus, Vibrio anguillarum, Vibrio harveyi, Vibrio parahaemolyticus, Yersinia ruckeri*, Virus WSSv, *Francisella noatunensis, Campylobacter jejuni, Chlamydia psittaci, Clostridium botulinurn, Clostridium perfringeus, Escherichia coli, Erysipelothrix rhusiopathiae, Haemophilus paragallinarum, Listeria monocytogenes, Mycobacterium avium, Mycoplasma gailisepticum, Mycoplasma synoviae, Pasteurella multicoda, Pseudomonas aeruginosa, Riemerella anatipestier, Salmonella enterica, Staphylococcus aureus, Staphylococcus hyicus, Streptococcus bovis, Yersinia pseudotuberculosis, Salmonella* spp, and *Brachyspira* spp.

Advantageously, the invention relates to the aforementioned composition for the aforementioned use thereof, in which the bacterial composition comprises:
- at least one of the following three strains of *Bacillus subtilis*: NOL01, NOL02, NOL03, said strains being deposited at the CNCM under respective numbers: CNCM I-4606, CNCM I-5043 and CNCM I-4607, and
- at least the *Lactococcus* lactic spp *lactis* 1 strain of lactic acid bacterium, strain NOL11, said strain being deposited at the CNCM under number CNCM I-4609.

The invention relates to the use of at least one strain chosen from strains NOL01, NOL02 and NOL03 and at least strain NOL11. The invention therefore relates to the following seven combinations:
NOL01 and NOL11,
NOL02 and NOL11,
NOL03 and NOL11,
NOL01, NOL02 and NOL11,
NOL01, NOL03 and NOL11,
NOL02, NOL03 and NOL11, and
NOL01, NOL02, NOL03 and NOL11.

All of these strains have been deposited in the national collection of microorganisms (CNCM) at the Institut Pasteur in Paris, under the Budapest Treaty.

Advantageously, the invention relates to the aforementioned composition for the aforementioned use thereof, said composition comprising from $10^4$ to $10^{11}$ bacterial colonies of *Bacillus* and from $10^4$ to $10^{11}$ bacterial colonies of lactic acid bacteria, the bacterial colonies being per mL or g of composition.

Within the meaning of the invention, "bacterial strain" refers to all of the individuals (bacteria) resulting from successive subcultures of a bacterial colony. In addition, in the invention, a bacterial colony corresponds to a colony-forming unit (CFU).

In other words, in this advantageous embodiment, if the composition according to the invention is in liquid form, said composition will comprise from $10^4$ to $10^{11}$ bacterial colonies of *Bacillus* per mL of composition, for each of the strains when the composition comprises at least two strains, and from $10^4$ to $10^{11}$ bacterial colonies of lactic acid bacterium per mL of composition.

If, however, the composition according to the invention is dehydrated or nonaqueous, the composition will comprise from $10^4$ to $10^{11}$ bacterial colonies of *Bacillus* per g of composition, for each of the strains when the composition comprises at least two strains, and from $10^4$ to $10^{11}$ bacterial colonies of lactic acid bacterium per g of composition.

In the invention, from $10^4$ to $10^{11}$ bacterial colonies means: about $10^4$, about $5.10^4$, about $10^5$, about $5.10^5$, about $10^5$, about $5.10^6$, about $10^7$, about $5.10^7$, about $10^8$, about $5.10^8$, about $10^9$, about $5.10^9$, about $10^{10}$, about $5.10^{10}$ or about $10^{11}$ bacterial colonies.

One skilled in the art easily knows how to determine this number of bacterial colonies, in particular by counting, either manually (using a Malassez counting chamber) or by using an automatic cell counter, or by dilution, then seeding on agar and counting colonies.

Still more advantageously, the invention relates to the aforementioned composition for the aforementioned use thereof, where the strains of *Bacillus* are in sporulated form and/or in vegetative form.

The lactic acid bacteria are in turn still in vegetative form. Therefore, the composition according to the invention comprises at least one strain of *Bacillus* in sporulated form and at least one strain of lactic acid bacterium in vegetative form, or comprises at least one strain of *Bacillus* in vegetative form and at least one strain of lactic acid bacterium in vegetative form.

Advantageously, the invention relates to the aforementioned composition for the aforementioned use thereof, where said composition is placed in contact with said eggs by spraying, incubation, soaking, spreading or powder dusting.

Depending on the application method used, one skilled in the art will know how to choose the most appropriate equipment, and will in particular prefer a liquid composition for spraying, soaking or spreading and will favor a dehydrated composition for an application by powder dusting.

Advantageously, the invention relates to the aforementioned composition for the aforementioned use thereof, said composition further being in contact with the newborns having hatched from said eggs from said farmed oviparous animals and/or in contact with the food supplied to the newborns having hatched from said eggs from said farmed oviparous animals.

Advantageously, the invention relates to the aforementioned composition for the aforementioned use thereof, said composition further being spread in the environment where said eggs and said newborns having hatched from said eggs from said farmed oviparous animals are placed.

The application in the environment makes it possible to control and/or orient the bacterial flora of the environment of the land-based farmed animals by decreasing the pathogenic pressure. It can be done by nebulization or spraying of the rearing buildings, incorporation into the bedding, etc. Less contamination of the animals is observed because there are fewer pathogenic foci. Such an application acts on the pathogens living or surviving in the environment. The spreading modes in the environment are spraying, nebulization, covering of the surfaces with foams, soaking, dipping or powder dusting.

The spreading is generally done on the surfaces of the rearing area, primarily on the surfaces in direct or potential contact with the animals, preferably on cleaned and disinfected surfaces, after waiting the end of the remanence of the disinfecting products.

The spreading in the environment is done at least once after a depopulated period, after a cleaning/disinfection protocol or before arrival of the animals. It is particularly advantageous to perform a repeated application every week.

The application on the newborns and/or in the food can be combined with the application in the environment.

The application on the newborns makes it possible to control or orient the microbism of the animal by decreasing the pathogenic pressure. The application can be done by nebulization, spraying, soaking, misting, footbath, foam, dipping, depending on the area of the animal where it is desired to deposit the composition according to the invention. This generates less contamination of the animals, since there are fewer pathogenic foci directly on the animal.

It is advantageous to apply the composition on the animal at least once as soon as possible in the lifetime of the animal. Preferably, the application is repeated every week.

Advantageously, from $10^3$ to $10^9$ CFU per egg or newborn will be used for applications in species of fish or crustaceans and from $10^4$ to $10^{10}$ CFU per egg or newborn for applications in poultry.

In the invention, from $10^3$ to $10^9$ CFU means: about $10^3$, about $5.10^3$, about $10^4$, about $5.10^4$, about $10^5$, about $5.10^5$, about $10^6$, about $5.10^6$, about $10^7$, about $5.10^7$, about $10^8$, about $5.10^8$, about $10^9$ CFU. It is also possible to provide the composition according to the invention in the food of the newborns.

Still more advantageously, the invention relates to a composition for the aforementioned use thereof, said composition essentially consisting of:
the following three strains of *Bacillus subtilis*: NOL01, NOL02, NOL03, said strains being deposited at the CNCM under the respective numbers: CNCM I-4606, CNCM I-5043 and CNCM I-4607, and
the *Lactococcus lactis* spp *lactis* 1 strain of lactic acid bacterium, strain NOL11, said strain being deposited at the CNCM under number CNCM I-4609.

This combination is particularly advantageous and is described in the examples.

It is particularly advantageous for the composition to comprise the three aforementioned strains of *Bacillus sub-* *tilis* bacteria, in vegetative and/or sporulated form, and the aforementioned strain of lactic acid bacterium, in vegetative form Advantageously, the invention relates to the aforementioned composition for the aforementioned use thereof, where said farmed oviparous animals are birds, reptiles, and said composition is applied on the shell of the eggs of said birds or of said reptiles.

The particularly advantageous birds concerned in the context of the invention are farmed birds such as landfowl, in particular turkeys, chickens, guinea fowl, quail and pheasants, but also ducks, ostriches, pigeons, partridges and geese.

The reptiles considered in the invention are tortoises, certain snakes and crocodiles.

In the context of the aforementioned birds, the egg is covered by the composition according to the invention. This covering may be total or partial.

Advantageously, the invention relates to the aforementioned composition for the aforementioned use thereof, where said farmed oviparous animals are aquatic oviparous animals and said composition is dispersed in the water of the rearing tanks of said aquatic oviparous animals in order to be placed in contact with said eggs, or in order to be placed directly in contact with said eggs.

In this advantageous embodiment, the oviparous animals are aquatic oviparous animals such as farmed fish, salamanders, newts, toads, frogs, shellfish, in particular prawns, aquatic reptiles, such as certain snakes, and freshwater turtles.

Inasmuch as the eggs of the aquatic oviparous animals are in the water, the composition according to the invention that is applied on the eggs is in particular dispersed in the water of the tanks containing said eggs. As previously mentioned, what is important is for the egg to be in contact with the composition according to the invention, such that when the newborn leaves the egg, it is immediately in contact with the flora.

In the invention, a rearing tank refers to any structure used within a fish farm containing the eggs and the newborns.

Advantageously, the invention relates to the aforementioned composition for the aforementioned use thereof, where said at least one strain of a bacterium of the genus *Bacillus* and said at least one strain of lactic acid bacterium are used simultaneously, separately or spread out over time.

In a separate application, it is for example possible to provide a tank, the Bacilli according to the invention at one end of the tank, and the lactic acid bacterium at another end of the tank.

In an application spread out over time, it is possible first to apply either the Bacilli or the lactic acid bacterium, then after a determined length of time, to apply the other type of bacteria.

The invention will be better understood in light of the examples below, and the figures described hereinafter.

LEGEND OF THE FIGURES

The graph of FIG. 1 shows the cumulative mortality of fries after hatching in troughs in two tests (diamonds and squares) and in the control trough (triangles). This cumulative mortality is expressed in percentage of the number of eggs hatched as a function of time (in days).

The graph of FIG. 2 shows the same graph as FIG. 1, in which the pathological events have been mentioned. A: Very severe costiasis, B: Very severe septicemic flavobacteriosis/costiasis, C: Severe costiasis, and ID: Very severe costiasis.

FIG. 3 shows the average weight of the fries in the different lots. The x-axis shows the time in days, and the y-axis shows the average weight of the fries in grams. The diamond-shaped points show the average weights of the fries belonging to the control lot, the triangles show that of the lot which received soaking of the eggs followed by an application of the composition in the environment, and the circles show that of the lot having received soaking of the eggs followed by an application of the composition in the food.

FIG. 4 shows the cumulative mortality of the fries over time in the different lots. The x-axis shows the time in days, and the y-axis shows the mortality percentage. The diamond-shaped points show the mortality in the control lot, the triangles show the mortality in the lot having received soaking of the eggs followed by an application of the composition in the environment, and the circles show the mortality of the lot having received soaking of the eggs followed by an application of the composition in the food. The curves show the statistical models associated with the actual mortalities with, in thin dotted lines, the model of the control lot, in solid lines, the model of the lot receiving application by soaking of the eggs and in the environment, and lastly, in thick dotted lines, the lot for application by soaking of the eggs and in the food.

EXAMPLES

Example 1—Efficacy of the Application of the Composition on Rainbow Trout Fries by Soaking of the Eggs and in the Environment The aim of this test is to determine the efficacy of the composition according to the invention on rainbow trout fries. The composition was applied on the eggs and in the environment of the animals.

Protocol:

The experiment is conducted on a farm on a production line.

The line corresponds to 3 hatching troughs with 60,000 eggs per trough. One will serve as control and the other two will receive the applications of the composition.

Both types of application are done:

Soaking of the Eggs:

The eggs are soaked for 4 minutes in 2 L of river water for the control lot and in 2 L of river water mixed with a half-dose of product for the test lot.

A dose of composition according to the invention was prepared from two separate 20 mL vials:

Vial 1 containing Bacilli NOL01, NOL02 and NOL03, at a concentration of about $10^9$ CFU/mL of the 3 Bacilli, Vial 2, containing the Lactococci NOL11, at a concentration of about $10^9$ CFU/mL.

Spraying on the Environment:

The troughs and trays of the test lots are treated with 2 L of river water mixed with a half-dose of product each before being placed in the water.

This treatment was repeated just before hatching, at the end of hatching, at the end of vitelline resorption, then once per week until the transfer date of the fries into the grow-out area. For each of these treatments, the water of the 3 troughs is decreased as much as possible so as not to harm the health of the fries, then increased to its normal level after the treatment of the test troughs. The total length of the test is about 2 months, period between the arrival of the eggs on the rearing farm and the transfer of the fries. This makes for a total of about 10 treatments.

The spraying operations were done using a manual sprayer (garden sprayer type).

Measurements and Results

During the test, the daily mortality in the three troughs is read, the health events are also noted.

FIG. 1 shows that the cumulative mortality appears to be approximately equivalent between the various troughs until September 10, where a less significant increase in mortality is observed in the test troughs. The mortality gap between the test troughs and the control trough deepens even more around September 19. Ultimately, 3,000 fewer deaths are observed in the test troughs than in the control trough on August 21, or a drop in mortality of 20 to 25%.

These two dates correspond to health episodes that are a septicemic flavobacteriosis and a costiasis, as shown by FIG. 2.

The water diverted from the river arriving in the troughs being the same for all 3 troughs, the pathogenic pressure is also equivalent. These results therefore show that the application of the composition as mentioned above makes it possible to avoid the mortality of the fries during a health episode.

Conclusion

The application of the composition by soaking on the eggs followed by an application in the environment of the rainbow trout fries makes it possible to limit the impacts of a pathogenic pressure on the health of the fries.

Example 2—Efficacy of the Application of the Composition on the Rainbow Trout Fries by Soaking of the Eggs, and in the Environment or Via the Food The aim of this test is to determine the efficacy of the composition according to the invention on the rainbow trout fries. The application of the composition being done on the eggs, and in the environment of the animals or on the eggs and via the food.

Protocol:

The experiment is done on a rearing farm on a production line.

The line corresponds to 3 hatching troughs with 60,000 eggs per trough. One serves as control (trough 5) and the other two (trough 2 and trough 3) receive the applications of the composition according to the invention.

The performed applications are as follows:

Soaking of the Eggs:

The eggs were soaked for 5 minutes in 2 L of source water for the control lot and in 2 L of source water mixed with a half-dose of product for the test lots, as defined in example 1.

Application in the Environment:

Before filling the troughs with water:

Test trough 3: the day before the eggs arrive, the trough is filled with water with a dose of flora, then recirculated for 1 day.

After filling the troughs with water:

Test troughs 2, 3 and control trough 5: before each application, the water of the troughs is decreased as much as possible so as not to harm the health of the fries, then increased to its normal level after application of the flora in test trough 3.

Test trough 3: The walls of the trough that are not submerged in the water are sprayed with 1 L of spring water mixed with a half-dose of product.

This treatment is repeated just before hatching, at the end of hatching, at the end of vitelline resorption, then once per week until the transfer date of the fries into the grow-out area. The spraying operations were done using a manual sprayer (garden sprayer type).

Application in the Food:

Test trough 2: Once per week, as of the first day of feeding, a half-dose of flora will be mixed by hand in the food before feeding the fries. The flora will be incorporated into the food about 1 hour before distribution. The half-dose of flora will be mixed with the food in a bucket before distribution.

Measurements and Results

During the test, the daily mortality and the average weekly weight of the fries were read in each trough, as well as the health events.

| Average weight of the fries by trough (g) | | | | | | | | |
|---|---|---|---|---|---|---|---|---|
| | D27 | D34 | D41 | D48 | D55 | D62 | D69 | D75 |
| Trough 2 | 0.156 | 0.25 | 0.35 | 0.515 | 0.687 | 0.826 | 1.22 | 1.45 |
| Trough 3 | 0.161 | 0.25 | 0.34 | 0.495 | 0.644 | 0.704 | 1.16 | 1.4 |
| Trough 5 | 0.172 | 0.217 | 0.32 | 0.526 | 0.635 | 0.752 | 1.09 | 1.35 |

FIG. 3 shows that the application of said composition by soaking of the eggs and via the food or in the environment improves the average weight of the fries, with a gain at the end of hatching respectively of 7.4% and 3.7% additional weight compared to the fries in the control group.

FIG. 4 shows that the two lots with the application of said composition by soaking of the eggs and via the food or in the environment were less affected by the health episode that occurred at about 33 days in all of the troughs. This is reflected by a significantly lower mortality of the fries (between 12 and 16% lower mortality relative to the control lot).

Conclusion

The application of the composition according to the invention by soaking on the eggs followed by an application in the environment or in the food of the rainbow trout fries improves the weight gain of the fries and reduces the mortality of the animals.

Example 3—Poultry Application

Experiments on poultry (hen) eggs were done.

The invention is not limited to the described embodiments, and other embodiments will appear clearly to one skilled in the art.

The invention claimed is:

1. A method for the prevention of infections or the improvement of zootechnical performance levels in oviparous animals, comprising a step of placing in direct contact with the eggs of farmed oviparous animals, a composition essentially consisting of a mixture of:
   a. the following three strains of *Bacillus subtilis*: NOL01, NOL02, NOL03, said strains being deposited at the CNCM under the respective numbers: CNCM I-4606, CNCM I-5043 and CNCM I-4607, and
   b. the *Lactotoccus lactis* spp *lactis* 1 strain of lactic acid bacterium, strain NOL11, said strain being deposited at the CNCM under number CNCM I-4609.

2. The method according to claim 1, wherein said composition comprising from $10^4$ to $10^{11}$ bacterial colonies of *Bacillus* and from $10^4$ to $10^{11}$ bacterial colonies of lactic acid bacterium, the bacterial colonies being per mL or g of composition.

3. The method according to claim 1, wherein the strains of *Bacillus* are in sporulated form and/or in vegetative form.

4. The method according to claim 1, wherein said composition is placed in contact with said eggs by spraying, incubation, soaking, spreading or powder dusting.

5. The method according to claim 1, wherein said composition further being in contact with the newborns having hatched from said eggs from said farmed oviparous animals and/or in contact with the food supplied to the newborns having hatched from said eggs from said farmed oviparous animals.

6. The method according to claim 1, wherein said farmed oviparous animals are birds and said composition is applied on the shell of the eggs of said birds.

7. The method according to claim 1, wherein said farmed oviparous animals are aquatic oviparous animals and said composition is dispersed in the water of the rearing tanks of said aquatic oviparous animals in order to be placed in contact with said eggs, or in order to be placed directly in contact with said eggs.

* * * * *